United States Patent [19]

Binder et al.

[11] 4,314,896
[45] Feb. 9, 1982

[54] SYSTEM FOR MEASUREMENT OF SPECIFIC IONS, SUCH AS SODIUM

[75] Inventors: Ira Binder, New Rochelle; Horace A. Teass, Jr., Armonk, both of N.Y.

[73] Assignee: McNab Incorporated, Mt. Vernon, N.Y.

[21] Appl. No.: 234,997

[22] Filed: Feb. 17, 1981

Related U.S. Application Data

[63] Continuation of Ser. No. 57,698, Jul. 16, 1979, abandoned.

[51] Int. Cl.³ ............................................. G01N 27/30
[52] U.S. Cl. ........................... 204/195 R; 204/195 G; 204/195 F; 324/425; 324/438
[58] Field of Search .......... 204/195 R, 195 F, 195 G, 204/195 M, 195 L, 195 B, 1 A; 128/635; 324/425, 438, 450

[56] References Cited

U.S. PATENT DOCUMENTS

| | | | |
|---|---|---|---|
| 3,249,103 | 5/1966 | Woodhouse | 128/635 |
| 3,605,722 | 9/1971 | Riseman et al. | 128/635 |
| 3,796,642 | 3/1974 | Higashiyama et al. | 204/1 T |
| 3,882,011 | 5/1975 | Hines et al. | 204/195 R |
| 3,957,612 | 5/1976 | Niedrach et al. | 204/195 M |
| 4,016,063 | 4/1977 | Radnoti | 204/195 R |

OTHER PUBLICATIONS

Donald T. Sawyer et al., "Experimental Electrochemistry for Chemists", pp. 34–51 (1974).
Research Disclosure, #16113, pp. 29–39, Sep. 1977.

*Primary Examiner*—G. L. Kaplan
*Attorney, Agent, or Firm*—Peck & Peck

[57] ABSTRACT

A simplified system for practical use in the measurement of specific ion concentrations. A probe for introduction into a fluid stream to measure the ion concentration thereof and said probe comprising an ion sensitive electrode for immersion in a fluid stream in combination with an annular elongated electrode having a noble metal, such as one of the platinum group of metals, on an end surface thereof for immersion in the fluid stream. The combination of the ion sensitive electrode, and the annular elongated electrode having an end thereof with the noble metal is placed in the fluid stream to be measured and is electrically connected to a measurement and/or indicating instruments.

3 Claims, 2 Drawing Figures

SYSTEM FOR MEASUREMENT OF SPECIFIC IONS, SUCH AS SODIUM

This application is a continuation of Application Ser. No. 57,698 filed July 16, 1979 and now abandoned.

BRIEF SUMMARY OF THE INVENTION

The detection of specific ions, especially at low concentrations, has become of increasing interest in recent years, both as a laboratory investigative tool and then for commercial and industrial process control.

The sodium ion has been of special interest in this regard because of its natural occurence in body fluids, in sea water, and in smaller amounts even in highly purified water.

As long as the primary use was in the laboratory or in short-time in-vivo experiments, there was little problem in the use of the standard glass reference cells required to complete the measurement circuit.

However, with the advent of better water purifying and polishing methods, the measurement of ion contents, especially sodium, in boiler feed water, condensate return, industrial water systems, chemical process streams and the like, a need has developed for sturdy, reliable, long service life sodium ion measurement devices.

This has become even more desirable and necessary with the further development of ion exchange resins to remove salt and other corrosion producing chlorides. When such resins become loaded or are approaching their practical limit of absorption, typically the first ion to be released is the sodium ion.

Since the accurate detection of most specific ions, such as sodium, requires specific types of glass and internal composition, the basic range for improvement comes in the standard reference portion of the electrode, where the typical glass electrodes are fragile and of limited lifetime, and in the electronics of the measurement and display system.

One of the prime purposes in the development of this invention has been to reduce to as large a degree as possible the problems which have heretofore been inherent in the practical, commercial and industrial use of standard specific ion electrodes, such as sodium or hydrogen. In achieving this purpose we have designed a relatively simple, sturdy, reliable and long lifetime specific ion probe or cell system, which does not require either a "standard glass reference cell" or other external standard reference cell to complete the circuit. The probe of this invention produces a sufficiently large and reproducible output to be read or displayed through proper electronic circuitry.

This invention provides a simple, self-contained, relatively sturdy cell system or probe with specific ion and noble metal electrodes which are so arranged that they are directly immersed and used in commercial laboratory, industrial, marine, or boiler system fluid or process streams. The cell is adapted for use in temperatures from just above the freezing point of water to just below the boiling point of water. This measuring cell may be used over a wide range of pressures, including vacuum applications.

A primary object of this invention is to provide a specific electrode pair which includes a specific ion sensitive, glass tipped, electrode with a self-contained gel and a metallic (platinum group metal surface) reference electrode (containing no glass and no liquid or gel or moistened dry salt) to complete a measurement circuit to an electronic instrumentation and to give a stable, repeatable e.m.f. (millivoltage) dependent upon the concentration of the specific ion in question.

Additional objectives and advantages of the present invention will become more readily apparent to those skilled in the art when the following general statements and descriptions are read in the light of the appended drawings.

DETAILED DESCRIPTION

Figure 1:
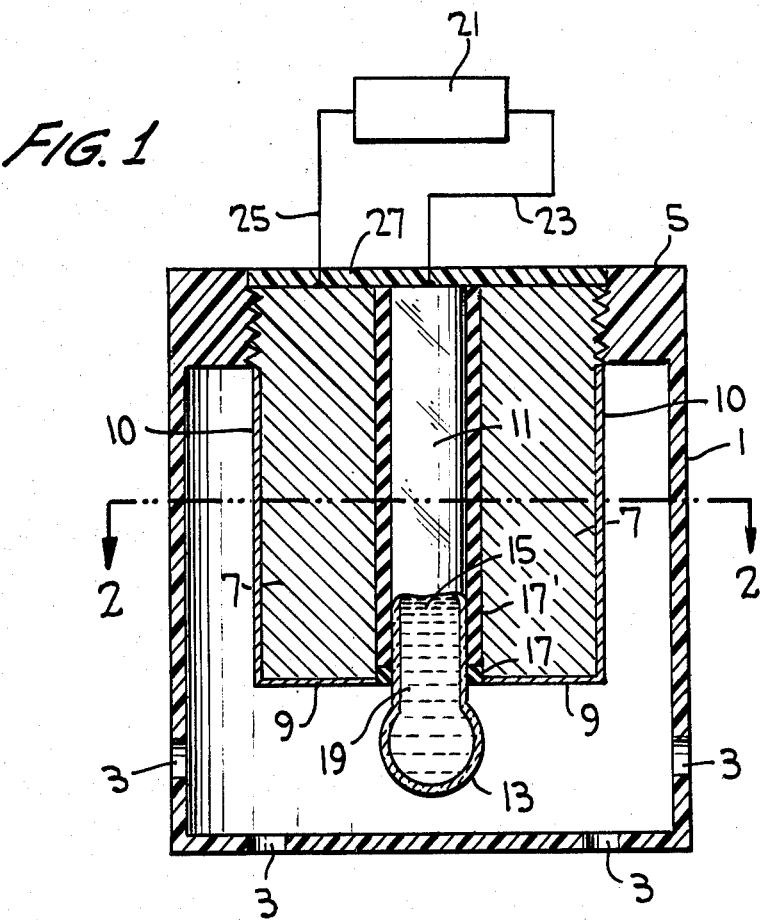
FIG. 1 is a sectional elevational view of the electrode system.
Figure 2:
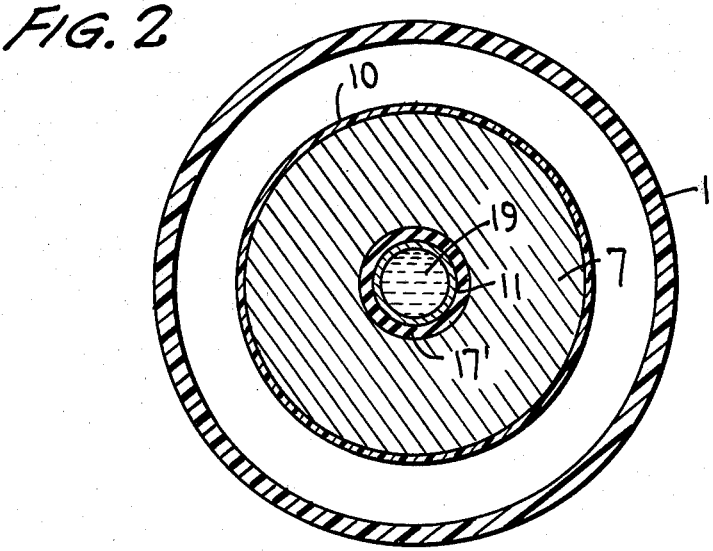
FIG. 2 is a view taken on the line 2—2 of FIG. 1.

In the accompanying drawing the numeral 1 designates an outer protective casing or housing for the electrodes which are immersed in the fluid stream. The casing 1 is a standard container, such as an insertion valve and may be provided with "O" ring seals, all as is well known in this art. The casing 1 is provided with a pluraliy of apertures 3 therein so that when the casing with the electrodes disposed therein is placed in a fluid stream the apertures 3 in the casing will allow the stream being measured to flow therethrough and come in contact with the two electrodes. The casing 1 may be attached to the electrode unit in any suitable and simple manner as by the threads 5.

The probe comprises an annular member 7 which is preferably made of brass or other conducting material and is formed as a one-piece member. On the lower end of the electrode 7 a noble metal surface 9 is provided and this surface may be made of, for instance, inert platinum or palladium. The entire circumferential wall of the electrode 7 is provided with any suitable insulating medium 10 in order to prevent the fluid stream from coming into contact with the brass or other conducting medium of the electrode member 7, the insulating medium 10 may comprise any non-conductor plastic, such as TFE.

Disposed within the annular one-piece conducting member 7 is an ion sensitive electrode 11 which, as will be apparent from consideration of the drawing, is of elongated configuration and extends below the noble surface 9. The end of the electrode 11 is preferably of bulbous shape as indicated at 13. This ion sensitive electrode, in this example, is a sodium ion sensitive electrode, and comprises a glass outer sheath 15 which permits the detection of the specific ion, largely to the exclusion of other competing ions. The specific ion electrode 11 is insulated from the conductor 7 by means of a non-conductive coating 17' and a rubber, or other elastomer, O ring 17 is provided. As will be understood by those skilled in this art, the specific ion sensitive electrode 11, in this example, contains a gel as of potassium chloride (KCl) 19. The specific ion electrode or probe 11 is connected to a high impedance meter 21 through conductor 23, while the electrode 7, with the noble metal surface 9, is connected to the opposite side of the meter 21 through the conductor 25. It is to be appreciated that the noble metal 9 and the brass, or the like, conductor 7 are insulated from the specific ion electrode 11 not only by the O ring 17 but also by an insulating cover 27. When the specific ion electrode 11 and the noble metal surface 9 are introduced into the fluid stream to be measured, the electrical path is completed and a voltage is produced across the probe, proportional to the concentration of the specific ion.

The glass outer sheath 15 permits preferential detection of the sodium ions (in the example) because of the specific range of the composition of the glass.

In certain cases the ion sensitive electrode, which in this example is a sodium sensitive electrode, will require prior preparation. This involves not allowing the electrode to become completely dry and having it sit in a moderately dilute, basic salt solution (i.e. 1000 ppm NaC1 at pH9) for one-half hour. This permits immediate response, whereas a dry electrode, or one stored in any pure deionized water will take several minutes to come to equilibrium, since the measuring action is a function of electronic charge diffusion through a glass wall. A generally similar process would be followed in connection with a hydrogen ion sensitive electrode, which also must not be allowed to dry out.

It is desirable to have the ion sensitive electrode extend into the fluid stream a distance below the noble metal surface 9, as this insures the solution contact with a representative, uniform sample of the solution. The bulbous construction at the end of the ion sensitive electrode 11 provides the greatest possible solution contact surface as well as body strength.

Thus, it can be appreciated that the invention provides the combination of a bulbous tipped specific ion sensor and a solid metallic reference electrode containing no gel, liquid moistened dried salt or the like. More particularly, the material composition of the specific electrode pair is important, that is, a specific ion sensitive, glass tipped electrode with a self-contained gel and a metallic (platinum group metal surface) reference electrode containing no glass and no liquid or gel or moistened dry salt to complete a measurement circuit to the electronic instrumentation.

What is claimed is:

1. A probe for use in the measurement of specific ion concentration in a fluid stream including, in combination, a specific ion sensitive electrode adapted to be immersed in the fluid stream and an annular elongated electrode having a solid body formed of a conductive material and having one end thereof coated with a noble metal, the annular elongated electrode adapted to be immersed in the fluid stream being measured, the annular elongated electrode having an inner circumferential wall and an outer circumferential wall, said inner circumferential wall providing a central area for receiving the ion sensitive electrode, insulation provided on the entire lengths of the interior and exterior circumferential wall surfaces of said annular elongated electrode insulating said circumferential wall surfaces from the fluid stream and from the specific ion sensitive electrode, said noble metal coated end surface of said annular elongated electrode being the sole part thereof which is adapted to be in contact with the fluid stream, the ion sensitive electrode adapted to extend into the fluid stream to a greater depth than the coated end surface of the annular electrode and a part of the end of the ion sensitive electrode which extends into the fluid stream being of bulbous configuration, said ion sensitive electrode including a glass tube, said glass tube providing a barrier for ions other than those the concentration of which is being measured in a fluid stream, and gel being contained in said glass tube, and electronic circuitry providing measurement instrumentation, said specific ion sensitive electrode and said annular elongated electrode being electrically connected thereto.

2. A probe in accordance with claim 1, wherein a casing is provided which is removably mounted on said annular elongated electrode and includes a depending portion spaced from the insulated length of said annular elongated electrode, said casing adapted to be immersed in the fluid stream, apertures in said casing for passage of the fluid stream therethrough, the probe in operative ion concentration measuring position immersed in the fluid stream within the casing.

3. A probe for use in the measurement of specific ion concentration in a fluid stream comprising an electrode pair composed of a specific ion sensitive glass tipped electrode with a self-contained gel and with the tip adapted to extend into the fluid stream and an annular metallic reference electrode having a central area for receiving the glass tipped electrode with the tip adapted to extend into the fluid stream to a greater depth than the annular electrode which is solid and devoid of any gel or the like and is coated with a platinum group metal surface.

* * * * *